(12) United States Patent
Van Engelen et al.

(10) Patent No.: US 6,416,772 B1
(45) Date of Patent: Jul. 9, 2002

(54) TOPICAL DERMAL ANAESTHETIC

(76) Inventors: H. Wayne Van Engelen; Patricia A. Van Engelen, both of 13921 W. Daimler Ct., Boise, ID (US) 83713

( * ) Notice: Subject to any disclaimer, the term of this patent is extended or adjusted under 35 U.S.C. 154(b) by 0 days.

(21) Appl. No.: 09/759,970

(22) Filed: Jan. 12, 2001

(51) Int. Cl.⁷ .......................... A61K 6/00; A61K 31/74
(52) U.S. Cl. ..................................... 424/401; 424/78.02
(58) Field of Search .............................. 424/522, 78.02, 424/400, 401; 514/390, 744, 937, 946, 947

(56) References Cited

U.S. PATENT DOCUMENTS

| | | | | |
|---|---|---|---|---|
| 4,477,469 A | * | 10/1984 | Herschler | 424/322 |
| 5,736,126 A | * | 4/1998 | Van Engelen et al. | 424/78.02 |
| 5,849,334 A | * | 12/1998 | Rivilin | 424/522 |

* cited by examiner

*Primary Examiner*—Jose' G. Dees
*Assistant Examiner*—Sharmila S. Gollamudi

(74) *Attorney, Agent, or Firm*—Kirton & McConkie; Michael F. Krieger

(57) ABSTRACT

A liquid composition applied transdermally for relief of pain comprising alcohol in an amount by weight of about 57 to about 91 percent; glycerin in an amount by weight of about 1 to about 12 percent; an analgesic agent in an amount by weight of about 2 to about 28 percent, the analgesic agent comprising a derivative of salicylic acid; methylsulfonylmethane in an amount by weight of about 0.02 to 5 percent; and emu oil in an amount by weight of about 0.01 to 3 percent, the liquid composition permeating skin to relieve pain. The composition further comprising, as an additional feature, aloe vera in an amount by weight of at least about 0.05 percent and having an amount by weight of about 0.05 to 4 percent. The composition features transdermal pain relief such that a patient can apply the analgesic agent directly to an area of pain without such side effects as stomach irritation which is normally associated with aspirin. The composition may be sprayed or rolled directly onto the painful area. Because of the unique formula, the composition is safe to vital internal organs, requires no mixing before use, and is shelf stable for marketing purposes.

13 Claims, No Drawings

TOPICAL DERMAL ANAESTHETIC

BACKGROUND

1. The Field of the Invention

The present invention relates to analgesics. Specifically, the present invention relates to an anagesic solution or liquid composition which is applied topically to the surface of the skin, or transdermally, for treatment of pain and irritation.

2. The Relevant Technology

The use of aspirin and other analgesic, anti-inflammatory agents is well known and has proven to be very valuable in the medical and scientific community. Aspirin has shown to have a variety of benefits in the treatment of aches and pains such as muscular aches, strains and cramps, arthritis, joint pain, lower back discomfort, bursitis, rheumatism, bums, insect bites and sports injuries.

However, certain side effects of aspirin, such as stomach irritation, may cause individuals to discontinue the use of this useful pain killer and anti-inflammatory. The ability to apply aspirin to an area of discomfort without ingesting the aspirin is a need which has been long felt within the medical community.

In addition, the ability to apply non-aspirin analgesics in an effective transdermal manner is a long-felt need. Applying an analgesic transdermally allows one to focus the analgesic in a certain painful area without diluting it by routing it through the blood stream.

A variety of difficulties, however, are associated with the goal of achieving a safe and stable form of transdermal analgesic. First, it is vital that the analgesic permeate the necessary layers of skin in order to anesthetize pain without adversely affecting vital internal organs. Thus, it is critical to provide a solution which dissolves aspirin or other analgesic agents and transports it topically to the area of pain where it can then permeate the skin to provide effective relief. While some topical analgesics have been introduced, they are largely limited in their ability to efficiently and effectively permeate the necessary layers of skin to provide for fast relief of the experienced pain.

Second, topical analgesics have been known to take effect long after they have been applied. Once the solution is applied to the skin, it usually takes quite some time for the analgesic to react and begin working. This may be caused by several reasons, such as the fact that the analgesic may not permeate the skin very well, the analgesic may need time itself to begin providing its pain relieving effects, etc.

Third, while certain solutions effectively cause the analgesic agents to permeate the skin, it is critical that the analgesic agent be stable within the solution such that it has a marketable shelf life. Aspirin is sparingly soluble in water. Permeating solutions may degrade aspirin and other analgesics by a variety of scientific processes including hydrolysis, glycolysis, and transesterification, for example. Until the present invention, teachings in the art indicated that aspirin was not stable in topical solutions involving the lower aliphatic alcohols because it too readily hydrolyzed to acidic and salicylic acids.

It would therefore be a significant advance in the art to discover and employ a composition having the ability to safely permeate skin at a more rapid rate. It would also be a significant advantage to provide a topical analgesic that is able to facilitate and speed up the pain relieving effects of the analgesic agent. Finally, it would also be a significant advantage to provide a topical analgesic that maintains a shelf stable state.

SUMMARY AND OBJECTS OF THE INVENTION

It is an object of the present invention to provide a topical analgesic having a composition that potentiates the analgesic, thus having a catalytic effect on the analgesic to speed and enhance pain relieving characteristics of composition.

It is another object of the present invention to provide a topical analgesic that relieves pain and does not dry the skin.

It is another object of the present invention to provide a composition which exists in a liquid state and is applied transdermally for relief of pain which contains an analgesic, anti-inflammatory agent which is shelf stable.

It is still another object of the invention to provide a composition containing absorption enhancing elements which allow the composition to permeate the necessary layers of the skin in order to address the aches and pains to be relieved, but does not enter the blood stream thus adversely affecting the internal organs.

It is a further object of the invention to provide such a solution which can be applied directly in the area of pain on the body.

It is still further an object of the invention to provide such a solution in a form which does not need to be shaken or stirred before use.

To achieve the foregoing objects, and in accordance with the invention as embodied and broadly described herein, the present invention features a liquid composition applied transdermally for relief of pain comprising: alcohol in an amount by weight of about 57 to about 91 percent; glycerin in an amount by weight of about 1 to about 12 percent; an analgesic agent in an amount by weight of about 2 to about 28 percent, the analgesic agent comprising a derivative of salicylic acid; methylsulfonylmethane in an amount by weight of about 0.02 to 5 percent; and emu oil in an amount by weight of about 0.01 to 3 percent, the liquid composition permeating skin to relieve pain. The liquid composition further comprises, as an option, aloe vera in an amount by weight of at least about 0.05 percent and being present in an amount by weight of about 0.05 to 4 percent, and in a preferred embodiment being present in an amount by weight of 0.125 percent.

In addition, and also as an optional element, allantoin may be used. Allantoin is a great potentiator and a good analgesic in its own right. The range of allantoin should be 0.04 to 2.00 percent by weight.

In a preferred embodiment, the analgesic agent consists of acetylsalicylic acid, triethanolamine, triethanolamine salicylate, acetaminiphen, (4-isobutylphenyl) propionic acid, naprosyn, and/or a salicylate. These may be used separately, or in conjunction with one another depending on the type of pain and desired relief. Also in a preferred embodiment, the alcohol consists of either isopropyl alcohol or ethyl alcohol.

In a preferred embodiment using triethanolamine or triethanolamine salicylate as the analgesic agent, the specific composition of the liquid formula is: alcohol present in an amount by weight of 81.7 percent; glycerin present in an amount by weight of about 3.12 percent; an analgesic agent present in an amount by weight of about 15 percent; aloe vera present in an amount by weight of 0.125 percent; methylsulfonylmethane present in an amount by weight of 0.04 percent; and emu oil present in an amount by weight of 0.015 percent. The use of aloe vera is optional, but preferred. If desired it may be removed, thereby increasing the percent by weight of one of the other elements in the composition.

In another preferred embodiment using acetylsalicylic acid, acetaminiphen, naprosyn, (4-isobutylphenyl) propionic acid, or a salicylate such as methyl salicylate as the analgesic agent, alcohol is present in an amount by weight of 88.78 percent; glycerin is present in an amount by weight of about 4.87 percent; analgesic agent is present in an amount by weight of about 6 percent; aloe vera is present in an amount by weight of 0.2 percent; methylsulfonylmethane (MSM) is present in an amount by weight of 0.08 percent; and emu oil is present in an amount by weight of 0.07 percent. Again, the use of aloe is optional, but preferred and may be removed if desired.

The present invention further features a liquid composition applied transdermally for relief of pain comprising alcohol, glycerin, an analgesic agent, and either or both of methylsulfonylmethane and emu oil, each being present in a percent by weight.

Finally, the present invention features a method for relieving pain, the method comprising: applying a liquid composition to the skin surrounding an area of said pain wherein the liquid composition comprises alcohol in an amount by weight of about 57 to about 91 percent; glycerin in an amount by weight of about 1 to about 12 percent; an analgesic agent in an amount by weight of about 2 to about 28 percent; aloe vera in an amount by weight of at least about 0.05 percent; methylsulfonylmethane in an amount by weight of about 0.02 to 5 percent; and emu oil in an amount by weight of about 0.01 to 3 percent; and allowing the liquid composition to permeate the skin to relieve pain. A method is also featured in the present invention comprising the step of mixing the above elements, and their respective percent by weight, into a liquid composition.

Applicant has discovered that a composition of glycerin, alcohol, an analgesic agent, methylsulfonylmethane, emu oil, and optionally, aloe vera, sufficiently permeates the skin in order to effectively treat pain.

Alcohol, preferably ethyl or isopropyl alcohol, effectively dissolves the analgesic so that it can be absorbed through the skin. Glycerin, when employed in the proper percentages, acts as a stabilizer for the acetylsalicylic acid, triethanolamine salicylate, or other analgesic agent, such that the alcohol does not significantly affect the marketable shelf life of the composition. Glycerin also sufficiently disperses the analgesic agent such that the composition does not need to be shaken or stirred before topical use. Methylsulfonylmethane and emu oil help to facilitate the absorption of the composition into the skin and also, due to the pain relieving characteristics in and of themselves, potentiate the analgesic to increase the efficacy of the composition.

Because of its liquid, well dispersed nature, the composition may be sprayed or rolled on the area where pain or aching exists without ingesting the composition. The resulting solution is an effective liquid topical analgesic and anti-inflammatory agent which does not disturb the digestive system and which is shelf stable for at least 18 months. The solution is effective for the relief of aches and pains associated with, among other things, muscular aches, strains and cramps, arthritis, joint pain, burns, lower back discomfort, bursitis, rheumatism, insect bites, and sports injuries, athlete's foot, shingles, headaches, menstrual cramps, and tennis elbow.

An additional advantage of the topical solution is that the risk of overdose is entirely eliminated. Although the solution may provide four to six hours of pain relief and may permeate at least seven layers of skin to relieve pain, zero, or only negligible, microscopic amounts of the analgesic agent, permeate into the blood stream thereby making overdose highly improbable.

Since the pain relieving solution is concentrated at the area where pain is indicating, the solution may be more effective than an oral dose, which becomes diluted in the body. In addition, the pain relief begins within a matter of minutes, or even within 60 to 90 seconds. Because of the unique composition, the solution need not be shaken or stirred before use and may be applied, for example, with a non-aerosol pump spray.

These and other objects and features of the present invention will become more fully apparent from the following description and appended claims, or may be learned by the practice of the invention as set forth hereinafter.

DETAILED DESCRIPTION OF THE PREFERRED EMBODIMENTS

It will be readily understood that the elements of the present invention, as generally described herein, could be arranged and designed in a wide variety of different compositions. Thus, the following more detailed description of the embodiments of the composition and methods of the present invention is not intended to limit the scope of the invention, as claimed, but is merely representative of the presently preferred embodiments of the invention.

The present invention features a liquid composition applied transdermally for relief of pain and comprises alcohol in an amount by weight of about 57 to about 91 percent, glycerin in an amount by weight of about 1 to about 12 percent, an analgesic agent in an amount by weight of about 2 to about 28 percent, methylsulfonylmethane in an amount by weight of about 0.02 to 5 percent, and emu oil in an amount by weight of about 0.01 to 3 percent. The liquid composition further comprises, as an option, aloe vera in an amount by weight of at least about 0.05 percent and being present in an amount by weight of about 0.05 to 4 percent, and in a preferred embodiment being present in an amount by weight of 0.125 percent. Although included together in the composition above, methylsulfonylmethane and emu oil may also be used separately, thus creating varying compositions and respective percentages by weight. Moreover, it is possible to combine one type of analgesic agent with another, such as triethanolamine or triethanolamine salicylate and naprosyn to create varying pain relieving effects.

The mixing instructions for the formula are relatively simple. The elements alcohol, glycerin, an analgesic agent, and optionally aloe vera, are mixed together until dissolved. Once these elements are mixed, the emu oil is then added if desired.

To include Methylsulfonylmethane in the composition, the Methylsulfonylmethane is first dissolved in water. Methylsulfonylmethane does not dissolve in alcohol so it cannot be mixed in initially with the other elements of the composition. However, once Methylsulfonylmethane is dissolved in a liquid solution, it stays dissolved. As such, the Methylsulfonylmethane may be added to the composition after it has first been dissolved in another liquid solution allowing such. Methylsulfonylmethane is typically added last due to its properties and inability to dissolve in water.

The mixing in each embodiment is preferably carried out at a high speed in a stainless steel container. In another method, alcohol is first mixed with the analgesic agent, such as aspirin, for about 20 minutes, after which glycerin is added and mixed for about 10 minutes, after which aloe vera is added, if desired, and mixed for about 30 minutes, followed by the addition of emu oil and Methylsulfonylmethane. Still another method, alcohol is mixed with glycerin for approximately 10 minutes, after which the analgesic agent is added and mixed for approximately 30 minutes, after which aloe vera, if desired is added and mixed for about five to about fifteen minutes, followed by the addition of Methylsulfonylmethane and emu oil.

The presence of alcohol in the composition is important because it readily dissolves the analgesic agent and assists in allowing the analgesic agent to permeate the skin. Alcohol also acts a good solvent for aspirin and other analgesics. The composition of the present invention has proven to permeate at least seven layers of skin. While isopropyl and ethyl alcohol are preferred, any alcohol having similar permeability and dissolution qualities may be employed in applicant's formula. Moreover, grade USP anhydrous alcohol is preferred. In the most preferred embodiment, a prescription grade of isopropyl alcohol is employed which is approximately 99.8 percent pure.

Glycerin acts as a stabilizer, preventing the alcohol from deactivating the analgesic effect of the analgesic agent and allowing the analgesic to remain in solution such that the composition does not need to be shaken before use, even after months on the shelf.

The analgesic agent is the active ingredient providing the pain relieving effects. Acetylsalicylic acid and triethanolamine salicylate are the preferred analgesics. However, it is possible that the analgesic agents may include one or a combination of ibuprofen, naprosyn, acetaminophen, and any other salicylates such as methyl salicylate, in addition to the preferred analgesic agents of acetylsalicylic acid and triethanolamine salicylate. These analgesic agents are powerful, proven pain killers, while including anti-inflammatory effects as well. When triethanolamine salicylate is employed, it is often added in higher quantities because of its weaker strength than aspirin. USP grades of acetylsalicylic acid, triethanolamine salicylate, and glycerine are used excusively.

The present invention also utilizes methylsulfonylmethane and emu oil in its composition. Methylsulfonylmethane and emu oil have been recognized as pain relievers in their own right. Indeed, Methylsulfonylmethane and emu oil have been reported as providing temporary relief of arthritis, asthma, inflamation, back pain, muscle cramps, muscle spasms, etc. Methylsulfonylmethane and emu oil have also been reported to aid in the healing of muscles and wounds, improve flexibility, and provide faster and better healing from surgical procedures.

In addition to their pain and wound relieving characteristics, Methylsulfonylmethane and emu oil are utilized in the composition to potentiate the analgesic element of the composition, which means that they act as a catalyst to facilitate faster, more efficient, and enhanced pain relief, thus greatly increasing the efficacy of the composition. Aloe vera also potentiates the analgesic to a certain extent. With the addition of Methylsulfonylmethane and emu oil, these two elements not only potentiate the analgesic while possessing pain relieving characteristics themselves, but they also, particularly the emu oil, do not overly dry or dehydrate the skin as the composition tends to do without the addition of Methylsulfonylmethane, emu oil, or even aloe vera. However, the two are independent of one another and may be used separately to alter the effects of the composition. In the preferred embodiment however, as emu oil and Methylsulfonylmethane increase the efficacy of the composition, these two elements together provide for an optimal composition.

Methylsulfonylmethane also facilitates the absorption of the composition into the skin once applied. As such, the areas of pain are more quickly and more efficiently reached. Faster absorption into the skin is another factor contributing to the overall increased efficacy of the composition.

Aloe vera, another proven pain reliever, may be employed on an optional basis to increase the pain relieving qualities of the composition.

A preferred method of use is to direct a spray of approximately 0.337 ml approximately one inch away from the skin at the location of pain. Three of such sprays should be liberally applied, after which the composition should be massaged until dry. After sixty seconds or so, the process should be repeated, followed by still another application sixty seconds later if necessary. These delayed re-applications are recommended in light of the fact that if one sprays several sprays all at once, the composition may not have sufficient time to permeate the skin and may run. For comfort reasons, it is recommended that contact with mucous membranes is avoided as stinging may result.

The foregoing description, and the methods of use and manufacture illustrated and described above relate to the varying formulas possible and as taught and claimed herein. Specifically, the ranges of each ingredients is provided for so that the most effective formula for relief may be created. While several possible combinations and percentages by weight are possible, each share some important characteristics unique to the present invention.

Each possible composition provides point relief of pain. Each composition is capable of being applied topically and has at least a comparable pain relieving effect as orally ingested aspirin, yet avoiding the gastric irritation or side effects associated with orally ingested aspirin.

The compositions containing acetylsalicylic acid, as a result of the topical application of the composition, significantly reduces the amount of salicylic acid introduced into the blood stream. The reduction is such that the actual amount of salicylic acid introduced into the blood stream through topical application is negligible compared to the amount introduced into the blood by orally ingested aspirin. Each composition disclosed herein is one that provides transdermal pain relief without digestive side effects, and is one that may be applied without first being shaken or stirred.

Each composition provides a pain relieving effect and may be applied directly to the skin surrounding a specific painful location in the body. In addition, each of the compositions disclosed herein possess an effective. shelf life of at least eighteen months. Furthermore, each composition will permeate at least seven layers of skin to relieve pain without creating digestive side effects. When employing the compositions and methods of applying as disclosed herein, pain relief often begins within about one or two minutes.

The following Examples demonstrate the results of experiments employing a test solution comprising: isopropyl alcohol in an amount by weight of about 81.7 percent, glycerin in amount of by weight of about 3.12 percent, triethanolamine salicylate in an amount by weight of about 15.0 percent, aloe vera in an amount by weight of about 0.125 percent; Methylsulfonylmethane in an amount by weight of about 0.04 percent; and emu oil in an amount by weight of about 0.015 percent ("hereinafter referred to in the examples as the "test solution"), a representative sample of the various compositions possible. These examples demonstrate the safety and usefulness of each of the formulas described herein.

EXAMPLE 1

Seventy-five people were tested. The object of the test was to determine whether the test solution of the preferred embodiment, as disclosed herein, provided for faster and better pain relieving results than other topical analgesics. Each of the subjects tested indicated that the test solution of the present invention out performed its counterpart compositions. The test solution was absorbed quicker into the skin, thus allowing the analgesic to more quickly and efficiently alleviate the area of pain. In addition the test solution provided for enhanced pain relieving effects while not overly dehydrating the area of skin where it was applied.

EXAMPLE 2

The test solution was applied to the skin of a woman with a headache. Minutes later the pain from the headache had subsided. She was able to then continue on with her daily routine free of headache pain.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. A liquid composition applied transdermally for relief of pain, said composition comprising:

alcohol in an amount by weight of about 57 to about 91 percent;

glycerin in an amount by weight of about 1 to about 12 percent;

an analgesic agent in an amount by weight of about 2 to about 28 percent, said analgesic agent comprising a derivative of salicylic acid;

methylsulfonylmethane in an amount by weight of about 0.02 to 5 percent; and emu oil in an amount by weight of about 0.01 to 3 percent, said emu oil and said methylsulfonylmethane potentiating said analgesic, said liquid composition permeating skin to relieve pain.

2. The liquid composition of claim 1, further comprising aloe vera in an amount by weight of at least about 0.05 percent.

3. The liquid composition of claim 2, wherein said aloe vera is in an amount by weight of about 0.05 to 4 percent.

4. The liquid composition of claim 3, wherein said aloe vera is in an amount by weight of 0.125 percent.

5. The composition of claim 1, wherein said alcohol in an amount by weight of about 57 to about 91 percent is selected from the group consisting of isopropyl alcohol and ethyl alcohol.

6. The composition of claim 1, wherein said analgesic agent in an amount by weight of about 2 to 28 percent is selected from the group consisting of acetylsalicylic acid, triethanolamine, triethanolamine salicylate, acetaminiphen, (4-isobutylphenyl) propionic acid, naprosyn, and a salicylate.

7. The composition of claim 2, wherein said alcohol is present in an amount by weight of 81.7 percent; said glycerin is present in an amount by weight of about 3.12 percent; said analgesic agent is present in an amount by weight of about 15 percent and comprises triethanolamine salicylate; said aloe vera is present in an amount by weight of 0.125 percent; said methylsulfonylmethane is present in an amount by weight of 0.04 percent; and said emu oil is present in an amount by weight of 0.015 percent.

8. The composition of claim 2, wherein said alcohol is present in an amount by weight of 88.78 percent; said glycerin is present in an amount by weight of about 4.87 percent; said analgesic agent is present in an amount by weight of about 6 percent; said aloe vera is present in an amount by weight of 0.2 percent; said methylsulfonylmethane is present in an amount by weight of 0.08 percent; and said emu oil is present in an amount by weight of 0.07 percent, said analgesic agent selected from the group consisting of acetylsalicylic acid, acetaminiphen, naprosyn, (4-isobutylphenyl) propionic acid, triethanolamine salicylate, and methyl salicylate.

9. A liquid composition in a form of a solution that does not need to be shaken or stirred before use and is applied transdermally for relief of pain, said composition comprising alcohol in an amount by weight of about 57 to about 91 percent;

glycerin in an amount by weight of about 1 to about 12 percent;

an analgesic agent in an amount by weight of about 2 to about 28 percent, said analgesic agent comprising a derivative of salicylic acid;

methylsulfonylmethane in an amount by weight of about 0.02 to 5 percent; and emu oil in an amount by weight that is less than the amount of the analgesic agent, said emu oil and said methylsulfonylmethane potentiating said analgesic, said liquid composition permeating skin to relieve pain.

10. A method for providing a liquid composition in a form of a solution that does not need to be shaken or stirred before use and is applied transdermally for relief, the method comprising the steps for:

dissolving alcohol, glycerin, and an analgesic agent to obtain a first composition, wherein the amount of the amount is about 57 to about 91 percent by weight, the amount of the glycerin is about 1 to about 12 percent by weight, and the amount of the analgesic agent is about 2 to about 28 percent by weight;

dissolving methylsulfonylmethane in water to obtain a second composition, wherein the amount of the methylsulfonylmethane is about 0.02 to 5 percent by weight; and combining the first composition, the second composition and an amount of emu oil to obtain a liquid composition in a form of a solution that does not need to be shaken or stirred before use and is configured to be applied transdermally for relief.

11. A method as recited in claim 10, wherein the analgesic agent comprises a derivative of salicylic acid.

12. A method as recited in claim 10, wherein the amount of emu oil is less than the amount of the analgesic agent.

13. A method as recited in claim 10, wherein the amount of emu oil is about 0.01 to 3 percent by weight.

* * * * *